United States Patent [19]

Harris et al.

[11] Patent Number: 4,511,163

[45] Date of Patent: Apr. 16, 1985

[54] ADAPTABLE TIP TUBING CONNECTOR

[75] Inventors: Nancy T. Harris; Leonard C. Harris, both of West Boro, Mass.

[73] Assignee: Mead Johnson & Company, Evansville, Ind.

[21] Appl. No.: 398,464

[22] Filed: Jul. 14, 1982

[51] Int. Cl.³ .............................. F16L 25/00
[52] U.S. Cl. .................... 285/177; 285/423; 285/DIG. 16; 604/257; 604/283; 604/905
[58] Field of Search ............. 285/177, 239, 260, 259, 285/423, DIG. 16; 604/93, 349, 350, 257, 283, 905

[56] References Cited

U.S. PATENT DOCUMENTS

| | | |
|---|---|---|
| 3,100,490 | 8/1963 | Desautels . |
| 3,307,552 | 3/1967 | Strawn . |
| 3,339,551 | 9/1967 | Stoutenburgh .................. 604/349 |
| 3,707,972 | 1/1973 | Villari et al. .................. 285/260 X |
| 3,731,684 | 5/1973 | Spiegel . |
| 3,767,233 | 10/1973 | Hodge . |
| 3,830,241 | 8/1974 | Dye et al. . |
| 3,831,600 | 8/1974 | Yum et al. . |
| 3,990,547 | 11/1976 | Barton . |
| 4,022,205 | 5/1977 | Tenczar . |
| 4,133,312 | 1/1979 | Burd . |
| 4,261,339 | 4/1981 | Hanson et al. . |
| 4,337,770 | 6/1982 | Young et al. .................. 604/93 X |

FOREIGN PATENT DOCUMENTS 1297060 5/1962 France .................. 285/177

Primary Examiner—Dave W. Arola
Attorney, Agent, or Firm—Richard P. Ryan; Robert H. Uloth

[57] ABSTRACT

An improved tubing connector with a connecting tip designed to adapt all sizes of tubing commonly employed in nasogastric and gastrostomy feeding. This tubing connector comprises a one-piece hollow unit having at one end a smooth tapered sleeve with an outer concentric shielding member which end serves as means for permanent attachment to a standard sized supply tube such as an out-dwelling tube attached to a reservoir; and at the other end, representing the adaptable connecting tip, an outwardly flared portion where the flaring is accomplished first by smooth taper in the tip end area and then by multiple tapered flanges of increasing diameter as distance from the tip end lengthens. This novel embodiment of adaptable connecting tip features permits a secure fit regardless of tubing size, but with ease of connection and disconnection. These characteristics are highly desirable for use with indwelling surgical tubing which requires delicate manipulation.

5 Claims, 7 Drawing Figures

ADAPTABLE TIP TUBING CONNECTOR

BACKGROUND OF THE INVENTION

Devices serving as connectors for flexible tubing have been heretofore provided and described in patent literature. Previously disclosed connectors usually effect a firm fit by making use of a connecting portion of generally conical shape, with or without stepped flanges of increasing diameter, which connecting portion is inserted longitudinally into the tubing bore for a given distance which results in sufficient stretching of the tube's circumference causing a snug grip on the outer periphery of the connector by the tube's internal surface.

Desaultels in U.S. Pat. No. 3,100,490, issued Aug. 13, 1963, disclosed a surgical drainage tube which employed a catheter adapter with a smooth tapered tip that flared outwardly as the distance from the end of the tip increased.

Strawn in U.S. Pat. No. 3,307,552, issued Mar. 7, 1967, discloses catheter tubing plugs employing conically shaped plug means which functionally engage the internal walls of the catheter tubing when pressed into the tube's longitudinal bore. This frictional engagement may be increased, according to Strawn, by providing a plurality of stepped frictional elements or spaced ring memnbers.

Hodge in U.S. Pat. No. 3,767,233, granted Oct. 23, 1973, discloses a coupling device for joining flexible tubing. This connector unit is of generally semi-cylindrical contour tapering from midsection to a lesser dimension at the ends, the outer surfaces of the tapered portions being provided with a plurality of projections to form surface irregularities for gripping the inner tubing surfaces. These surface irregularities are described by Hodge as suitably being a series of frustoconical sections of progressively increasing size from the ends toward the midsection.

Both Dye, et al., U.S. Pat. No. 3,830,241, issued Aug. 20, 1974 for a vented adapter and Yum, et al., U.S. Pat. No. 3,831,600, issued Aug. 27, 1974 for a variable fluid flow control, utilize tubing connectors with stepped surface irregularities.

The following patents disclose connectors utilizing tapered sleeves for engaging flexible tubing.

Barton, U.S. Pat. No. 3,990,597, issued Nov. 9, 1976 for a container and gavage tube adapter with vent.

Tenczar, U.S. Pat. No. 4,022,205, issued May 10, 1977 for fluid connectors.

Hanson, et al., U.S. Pat. No. 4,261,339, issued Apr. 14, 1981 for a balloon catheter with rotatable support.

Burd, U.S. Pat. No. 4,133,312, issued Jan. 9, 1979 for a connector for attachment of blood tubing to external arteriovenous shunts and fistulas.

The Burd patent discloses a universal connector for a blood tubing set employing a sleeve-like tip which relies on both its external and internal taper for a wide range of tubing adaptability. Additionally, a locking means is disclosed for prevention of accidental disengagement of the tubing. This has been a common problem especially for connectors which are designed to fit a broad range of tubing sizes.

Equally troublesome, especialy in clinical situations, is the reverse problem: ease of disconnection.

Spiegel in U.S. Pat. No. 3,731,648, granted May 8, 1973, described a hinged connector interposed between the catheter and an inlet-outlet tube in an irrigation and urinary drainage apparatus which could be closed or opened without disconnection of any elements of the system. This connector couples the cathether by means of an insertable tip with an exterior shell of frusto-conical configuration having a series of ribs disposed abut its circumference. The advantage of uncoupling a hinged connector to open the system is described in the patent specification as avoiding the difficulties in removing the semirigid tip from the flexible rubber catheter tubing which " . . . requires use of a pulling and twisting motion and separation is often so abrupt and violent that . . . there is a danger of accidentally pulling on the catheter itself and causing discomfort or even trauma to the patient . . . ."

There are, however, applications in which disconnection is required as for attachment of a new supply container for example when tube feeding patients. One objective then, of the present invention, was to make a connector that provided a secure leak-proof fit but that was also easy to disconnect. A second objective was to make an adaptable connector that could provide this type of fit to a wide variation in tubing sizes ranging from very small tubes used in nasogastric intubation of infants to large gastrostomy tubes placed in adults. The connector of the instant invention realizes these objectives by virtue of construction of its adaptable tip, which differs from connectors previously disclosed by incorporating a smooth tapered surface near the tip end for connecting with smaller tubing and further from the tip end, a surface with stepped frictional rings for connecting with larger tubing.

SUMMARY OF THE INVENTION

This invention provides a universal connector for joining a container for delivery of a liquid dietary to a patient access tube such as a nasogastric or gastrostomy tube. It is intended that this connector be provided with pre-filled containers which are normally employed in hospital use since the sterile dietary need not be transferred to another container prior to use, thus minimizing required hospital labor and reducing the possibility of contamination.

The connector of this invention is simple, easy to manufacture and provides an improved adaptable tip designed for pressure-fit connections with a wide range of tubing sizes commonly employed in liquid dietary feeding.

The connector of the present invention is preferably of unitary construction formed from moldable plastics. The supply container end of the unit is comprised of a smooth tapered sleeve surrounded by a peripheral shield portion of the unit. This end serves as means for permanent attachment to a standard size supply tube such as any out-dwelling tube attached to a reservoir. The other end of the connector which is the adaptable tip is comprised of a smooth tip end portion, representing about a third of the length of the connector and a flanged base end portion, representing about a third the length of the connector. This novel combination of the smooth tip end portion and the flanged base end portion provides the adaptability characteristic of the connector so that it can be firmly attached to in-dwelling tubing of varying size but yet easily connected and disconnected.

The novel arrangement of these parts and features of construction will become apparent from the following description taken in conjunction with the drawings illustrating a preferred embodiment.

DESCRIPTION OF THE DRAWINGS AND DETAILED DESCRIPTION OF THE INVENTION

Figure 1:
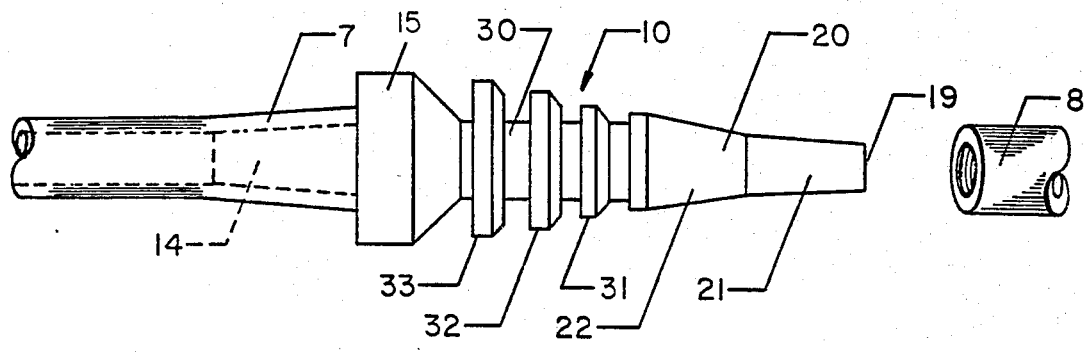
FIG. 1 is a view illustrating a connector already attached to an out-dwelling supply tube and ready for insertion into an in-dwelling patient feeding tube.
Figure 2:
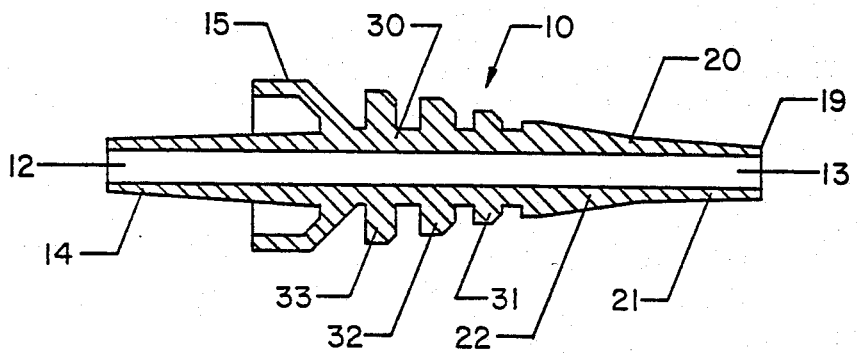
FIG. 2 is a cross-sectional view of the connector of this invention.
Figure 3:
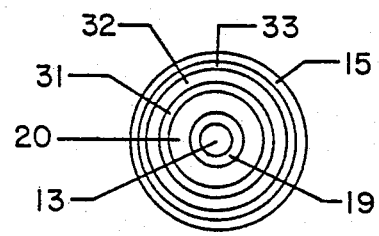
FIG. 3 is an end view of the connector of FIG. 2.

Referring to the drawings, the connector of this invention is most completely shown in FIG. 1 and FIG. 2 and is generally designated 10. Connector 10 consists of a body having a bore therethrough, which bore may be of constant diameter or preferably consists of a larger diameter portion 12 and a smaller diameter portion 13 in communication. Surrounding large diameter bore 12 is a tapered sleeve 14 with a size selected so as to snugly receive the inner wall surface of the end of a conventional supply tube 7, as shown in FIGS. 1, 4, 5, and 6 typically connected to a liquid diet feeding container. The tip end of supply tube 7 fits securely inside a surrounding peripheral shield member 15 and is normally secured therein by solvent softening of the mating surfaces and then pressing the parts together.

The connector 10 is preferably fabricated from a plastic which is susceptible to softening by the same solvent which softens the material used in the supply tube 7. In the event the material selected for connector 10 is not plastic, or is not a plastic softenable by the solvent which also softens the supply tube, attachment of the supply tube to sleeve 14 surrounded by peripheral shield member 15 at one end of connector 10 may be made by using an adhesive between the mating surfaces, or with various types of mechanical connectors well known to those skilled in this art.

Figure 4:
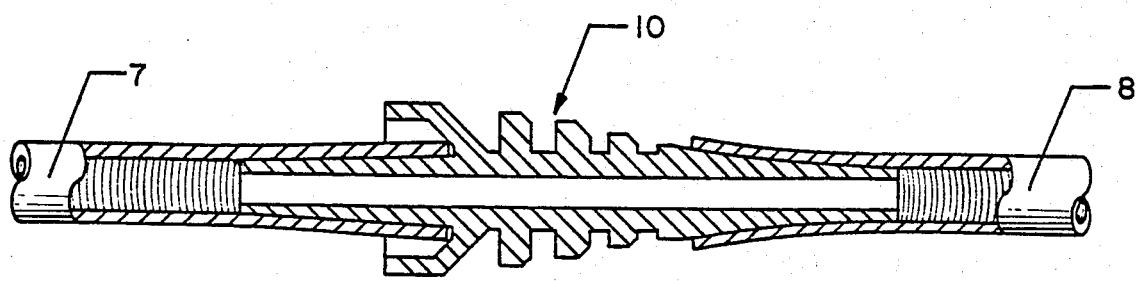
FIG. 4 is a view partly in section showing the connector joining an out-dwelling tube to a small in-dwelling tube.
Figure 5:
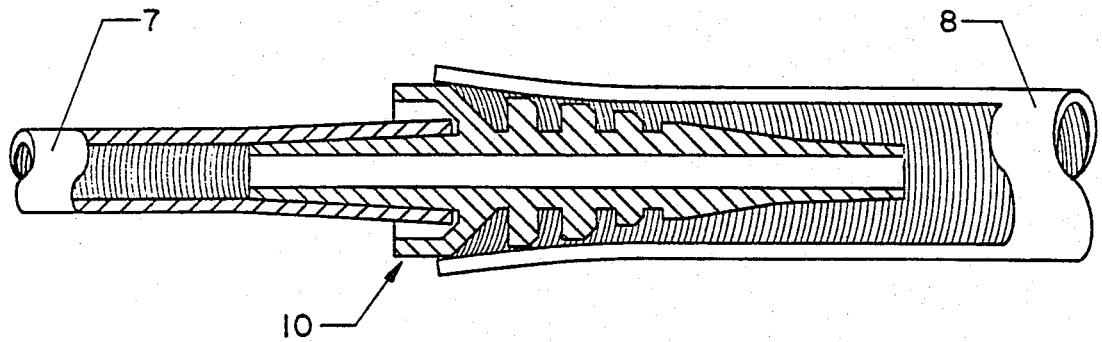
FIG. 5 is a view partly in section showing the connector joining an out-dwelling tube to a large in-dwelling tube.
Figure 6:
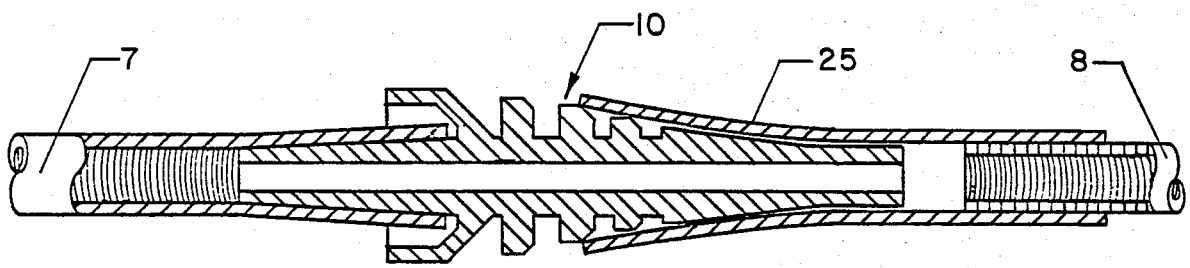
FIG. 6 is a view partly in section showing the connector joining an out-dwelling tube to an adapter which is fitted to a very small in-dwelling tube.

The adaptable connection end of connector 10, that is, the end 19 opposite from the end onto which the supply tube 7 is attached, contains the combination of inter-related and interfunctional means so located and arranged as to provide the improved adaptable connector construction that distinguishes this invention from heretofore known connectors in use in connection with tube feeding sets. Examples of the connector's adaptability are shown in FIG. 4: attachment to a small in-dwelling tube; FIG. 5: attachment to a large in-dwelling tube; and, FIG. 6: attachment via an adapter of the sort provided with very small in-dwelling tubes.

Figure 7:
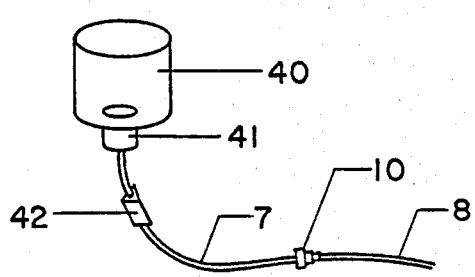
FIG. 7 is a front view showing a tube-feeding kit attached to an in-dwelling tube via the connector.

Illustrating the connector's usage with a conventional tube-feeding kit is shown in FIG. 7 where the in-dwelling tube 8, insertable in the patient, is connected to a liquid dietary supply tube 7 by the connector 10. The supply tube 7, in turn, is in communication with a liquid dietary containing reservoir 40 through a conventional drip chamber means 41. Supply tube 7 runs through a flow rate regulator means 42 which is located between drip chamber means 41 and connector 10.

Returning now to the novel construction of the adaptable connection end of connector 10, the connection end 19 is multifaceted, e.g., a tip end portion 20, representing from a quarter to a half and preferably about one-third of the overall length of connector 10, is a smooth surfaced sleeve tapered so that the outer diameter increases as distance from the tip 19 increases; and a flanged portion 30 with a multiplicity of flanges 31, 32, 33 which, in a preferred embodiment, are essentially beveled rings of progressively decreasing size from shield member 15 to tip section 20. The smooth tip portion 20 is itself divided into two parts of approximately equal length and these parts 21 and 22 possess differing rates of taper. The diameter of the tip end 19 of sleeve area 21 is less than one-tenth the total length of the connector, preferably 0.07 to 0.09 as great as the connector length. The flanged mid-portion 30 of the connector representing from a quarter to a half and preferably about one-third of the connector's length contains a multiplicity of stepped flanges 31, 32, 33 which increase in diameter by increments of 10% to 25% as distance from the tip 19 increases. Preferably, the diameter of each flange member 31, 32, 33, and shield member 15 increases from about 14% to 20% successively, this range also representing the preferred percentage increase in distance of each successive flange member from the tip 19. It should be understood that this invention embraces other embodiments in which spacing intervals between flanges may be constant or vary in a differing fashion.

The connector 10 will be utilized by gripping the peripheral shield 15 with the thumb and fingers of one hand while grasping the tubular means such as the catheter 8 and pressing the tip end 19 into the opening formed by the longitudinal bore until the outer surface of connector 10 frictionally engages the inner surface of tube 8 thereby retaining it in a joining process. The unique combination of structural features characterizing the adaptable connection end of the instant connector maximizes firm adaptive fit with in-dwelling tubes of varying size while at the same time maintaining relative ease in connecting and disconnecting the supply means for delivery of a liquid dietary.

Various changes and modifications in the coupling device herein disclosed may occur to those skilled in the art, and to the extent that such changes and modifications are embraced by the appended claims, it is to be understood that they constitute part of the present invention.

What is claimed is:

1. An improved adaptable tubing connector comprising a body having a fluid passageway therethrough and with a dietary supply tube connector at one end and an adaptable connector means at the opposite end of the body with the adaptable connector means further comprising a first means and a second means for a selective press-fit connection into and disconnection from the inner bore of an in-dwelling tube insertable into a patient for liquid tube feeding wherein the first means for selective connection comprises a sleeve member defining a tip end portion of said passageway, the outer end of the sleeve member projecting from said body, said sleeve member being defined by a wall, said wall having an outer surface which tapers gradually from its smallest diameter at its outer end to its largest diameter at its inner end at a rate of taper which becomes substantially greater at a point midway between the outer and inner ends; the second means comprises a middle portion of the connectors length, this middle portion having a multiplicity of stepped flanges which incrementally increase in diameter and spacing therebetween as distance from the tip end increases; the first and second means serving together to adaptably connect firmly via press-fit with tubing of varying size but to do so with ease of connection and disconnection.

2. The improved tubing connector of claim 1 wherein the stepped flanges are ring members which are beveled to facilitate frictional engagement with a mating surface, of the in-dwelling tubing and wherein a fluid-tight seal is effected by press-fit contact between said ring members and the inner bore surface of the in-dwelling tubing.

3. The improved tubing connector of claim 2 wherein the ring member diameters increase in size by increments ranging from about 10 to 25% as the distance from the tip end portion increases.

4. The improved tubing connector of claim 3 wherein the spacings between ring members increase by increments ranging from about 14 to 20% as the distance from the tip end portion increases.

5. The improved adaptable tubing connector as defined in claim 2 further including a liquid dietary reservoir to which said connector is adapted to be attached at said one thereof by a liquid dietary supply tube and wherein said connector is adapted to be connected at said opposite end thereof to an in-dwelling feeding tube.

* * * * *